United States Patent
Bette et al.

(10) Patent No.: US 7,850,718 B2
(45) Date of Patent: Dec. 14, 2010

(54) CONNECTING DEVICE FOR SPINAL OSTEOSYNTHESIS

(75) Inventors: Stephane Bette, Paris (FR); Dominique Petit, Verton (FR); Didier Thibout, Paris (FR); Gerard Vanacker, Saint-Maur (FR)

(73) Assignee: Spinevision, Paris (FR)

( * ) Notice: Subject to any disclaimer, the term of this patent is extended or adjusted under 35 U.S.C. 154(b) by 513 days.

(21) Appl. No.: 10/558,658

(22) PCT Filed: May 28, 2004

(86) PCT No.: PCT/FR2004/001330

§ 371 (c)(1),
(2), (4) Date: Apr. 17, 2006

(87) PCT Pub. No.: WO2004/107997

PCT Pub. Date: Dec. 16, 2004

(65) Prior Publication Data

US 2007/0043355 A1 Feb. 22, 2007

(30) Foreign Application Priority Data

May 28, 2003 (FR) .................................. 03 06523

(51) Int. Cl.
*A61B 17/70* (2006.01)
(52) U.S. Cl. ................... 606/267; 606/264; 606/266
(58) Field of Classification Search .................. 606/61,
606/250–253, 256–260, 264–272, 278
See application file for complete search history.

(56) References Cited

U.S. PATENT DOCUMENTS

| | | | | |
|---|---|---|---|---|
| 4,887,596 A | * | 12/1989 | Sherman | 606/305 |
| 5,098,432 A | * | 3/1992 | Wagenknecht | 606/54 |
| 5,167,661 A | * | 12/1992 | Wagenknecht | 606/54 |
| 5,176,680 A | * | 1/1993 | Vignaud et al. | 606/302 |
| 5,409,488 A | * | 4/1995 | Ulrich | 606/260 |
| 5,443,467 A | | 8/1995 | Biedermann et al. | |
| 5,752,957 A | * | 5/1998 | Ralph et al. | 606/266 |
| 5,944,719 A | * | 8/1999 | Leban | 606/59 |
| 6,146,383 A | * | 11/2000 | Studer et al. | 606/308 |
| 6,309,389 B1 | * | 10/2001 | Baccelli | 606/264 |
| 6,309,390 B1 | * | 10/2001 | Le Couedic et al. | 606/264 |
| 6,309,391 B1 | * | 10/2001 | Crandall et al. | 606/256 |
| 6,540,749 B2 | * | 4/2003 | Schafer et al. | 606/270 |
| 7,261,713 B2 | * | 8/2007 | Langmaid et al. | 606/59 |

(Continued)

FOREIGN PATENT DOCUMENTS

DE 41 07 480 A1 9/1992

(Continued)

*Primary Examiner*—Todd E Manahan
*Assistant Examiner*—Ellen C Hammond
(74) *Attorney, Agent, or Firm*—Bachman & LaPointe, P.C.

(57) ABSTRACT

A connecting device for spinal osteosynthesis has an osseous anchoring device, a connector that accommodates a joining shaft and is fixed to one end of the anchoring device, and a tightening device for immobilizing the joining shaft. The connecting device is characterized in that the connector is fixed to the anchoring device with the aid of a pin that penetrates the anchoring device and embodies a pivot joint. Furthermore, the device comprises an arrangement for stabilizing the connector relative to the anchoring device when the device is implanted in the patient, the stabilizing arrangement being located on the plane encompassing the shaft and the anchoring device.

26 Claims, 9 Drawing Sheets

U.S. PATENT DOCUMENTS

| | | | |
|---|---|---|---|
| 7,314,467 B2 * | 1/2008 | Howland | 606/86 A |
| 7,322,979 B2 * | 1/2008 | Crandall et al. | 606/256 |
| 2002/0035365 A1 * | 3/2002 | Kumar et al. | 606/61 |
| 2002/0173789 A1 * | 11/2002 | Howland | 606/61 |
| 2004/0210216 A1 * | 10/2004 | Farris et al. | 606/61 |

FOREIGN PATENT DOCUMENTS

DE  4107480 A1 * 9/1992

* cited by examiner

CONNECTING DEVICE FOR SPINAL OSTEOSYNTHESIS

BACKGROUND OF THE INVENTION (1) Field of the Invention

The present invention relates to the field of spinal osteosynthesis serving in spine surgery for correcting and stabilizing the spinal column.

The present invention relates more particularly to a connector device for spinal osteosynthesis, said connector device comprising osseous anchor means, a connector designed to receive a coupling rod and assembled to one end of the anchor means, and tightening means for immobilizing the coupling rod.

(2) Prior Art

Numerous systems are known in the prior art for correcting or stabilizing the spinal column.

German Utility Model DE 41 07 480 describes a bone screw designed to fasten a device for correcting and stabilizing the spinal column. For that purpose, that bone screw has a head provided with a semicircular recess zone for receiving the coupling rod. Said coupling rod is locked onto the head of the bone screw by a substantially U-shaped closure piece, said closure piece forming a clamp for clamping onto the head of said screw.

The problem that arises with that solution is that the rod is not tilt-stabilized in a plane containing the coupling rod and passing through the bone screw.

European Patent Application EP 0 614 649 also proposes a bone screw comprising a screw element having a threaded portion and a head that has a portion that is sphere segment in shape, and a cylindrical receiving piece that is designed to receive the head of the screw element and a bar that is to be assembled to the bone screw. The receiving piece is provided with a first bore situated at one of its ends and designed to allow the threaded portion of the screw element to pass through, with a hollow spherical portion designed for application to the head, and with an open second bore formed opposite from the first bore and designed for insertion of the threaded portion provided with the head. Said receiving piece also has a substantially U-shaped section having two free branches, each of which is provided with an external thread and with an internal thread. In said U-shaped section, the following are provided: a presser element acting on the head; a locking screw screwed in place in the open end, above the bar that is placed in the U-shaped section; and a lock nut screwed onto said external thread of the branches of said receiving piece.

Unfortunately, the prior art devices suffer from drawbacks. Firstly, the movements that are allowed on the bone screws remain relatively small, in particular in the frontal plane. This then results in manipulation difficulties, and in particular difficulties in assembling the coupling rods to the bone screws and in disassembling them therefrom. Secondly, during readjustment surgery, it can be difficult to unscrew the bone screw due to the drive means of the screw not being aligned with the head that receives the coupling rod.

SUMMARY OF THE INVENTION

An object of the present invention is to remedy the drawbacks of the prior art by proposing a connector device that makes it possible to increase the extent to which the connector holding the coupling rod can move on the anchor means used on the vertebrae.

An object of the present invention is thus to provide a device that makes manipulation easy, and more particularly that facilitates assembling the coupling rod to the anchor means and disassembling said coupling rod therefrom, and that facilitates unscrewing the anchor means during readjustment surgery.

To this end, the present invention is of the type described above and it is remarkable, in its broadest acceptation, in that the connector and the anchor means are assembled together by a pin passing through the anchor means, said pin constituting a pivot coupling, and in that the device has stabilization means for stabilizing the connector relative to the anchor means in the plane containing the rod and the anchor means, when implanted in the patient.

Preferably, the connector co-operates with said pin with a degree of rotation relative to the axial direction, and a degree of angular displacement relative to at least one perpendicular direction.

Advantageously, the connector co-operates with said pin with an amplitude of rotation relative to the axial direction lying in the range 90° to 180°, and the amplitude of angular displacement relative to at least one perpendicular direction lies in the range 20° to 60°.

Preferably, that portion of the pin which is designed to be disposed inside said anchor means presents convexity distributed uniformly over the circumference of said pin in order to enable said pin to move over an angular displacement on said anchor means relative to a direction perpendicular to said pin.

In a first embodiment of the invention, said stabilization means are constituted by the fact that said pin has an axial direction parallel to the axial direction of said coupling rod, allowing a degree of axial rotation only, to the exclusion of tilting in a plane perpendicular to the rod.

Advantageously, the portion of the pin which is designed to be disposed inside said anchor means presents convexity distributed uniformly over the circumference of said pin in order to enable said pin to move over a sagittal angular displacement on said anchor means.

In a first variant of the first embodiment of the invention, said connector has a bearing surface on which the coupling rod bears, said bearing surface being configured in a manner such as to enable said coupling rod to move over an additional sagittal angular displacement relative to said anchor means.

Advantageously, said bearing surface is convex in shape or consists of a cradle-forming element disposed in the connector, said cradle-forming element having a bottom recess co-operating with the connector in a manner such as to enable the additional sagittal angular displacement to take place, and a top recess designed to receive the coupling rod.

In a second variant of the first embodiment of the invention, an intermediate element receiving said coupling rod passes through the connector, said through intermediate element having a bottom recess co-operating with the end of said anchor means in a manner such as to enable all of the degrees of freedom of rotation of said device to be locked.

Advantageously, said through intermediate element has a top face of convex shape enabling said coupling rod to move over the sagittal angular displacement relative to said connector, or said through element consists of a cradle-forming through element enabling said coupling rod to move over the sagittal angular displacement relative to said connector.

Advantageously, the bottom recess of said through intermediate element presents at least one serrated or fluted zone. Similarly, the end of the anchor means is serrated or fluted over its entire surface or over a portion thereof.

In a second embodiment of the invention, said stabilization means are constituted by the fact that said pin has an axial direction perpendicular to the axial direction of said coupling rod, and in that the device further comprises locking means for preventing the connector from moving pivotally on said anchor means.

Preferably, that portion of the pin which is designed to be disposed inside said anchor means presents convexity distributed uniformly over the circumference of said pin in order to enable said pin to move over a frontal angular displacement on said anchor means.

Advantageously, the locking means consist of a piece passing through the connector, said through piece presenting a bottom face constituted by a recess co-operating with the end of said anchor means and a top face receiving said coupling rod, so as to enable all of the degrees of freedom of rotation of said device to be locked. In a first example of implementation, the through piece presents a top face that is convex in shape. In another example of implementation, the through piece consists of a cradle-forming element which, in its top face, has a recess for receiving said coupling rod.

Advantageously, the recess in the bottom face of said through piece is serrated or fluted at least in part. Similarly, the end of said anchor means that is in contact with the through piece is serrated or fluted at least in part.

Advantageously, said pin has longitudinal fluting over all or some of its surface.

Advantageously, said pin passes through the end of the anchor means and co-operates with two holes provided in branches of the connector, which holes present cross-sections complementary to the cross-section of the pin, said branches being disposed on either side of said pin.

Advantageously, the anchor means are constituted by a screw which has a threaded portion, and a spherical head provided with a cavity for receiving said cylindrical pin in part.

Advantageously, the connector is made up of a substantially U-shaped rod-receiving piece designed to receive one end of said anchor means as provided with the pin and with the coupling rod, and of a closure piece that comes to engage over the rod-receiving piece in order to hold the coupling rod onto the rod-receiving portion of said connector by using said tightening means.

The present invention also provides a system for osteosynthesis on the spinal column, in particular for stabilizing the vertebrae, said system comprising at least one coupling rod and at least two connector devices according to any preceding claim, each of said connection devices being suitable for being anchored in a respective vertebra.

BRIEF DESCRIPTION OF THE DRAWINGS

The invention will be better understood on reading the following description of an embodiment of the invention given merely by way of explanation and with reference to the accompanying figures, in which.

DETAILED DESCRIPTION OF THE PREFERRED EMBODIMENT(S)

Figure 1:
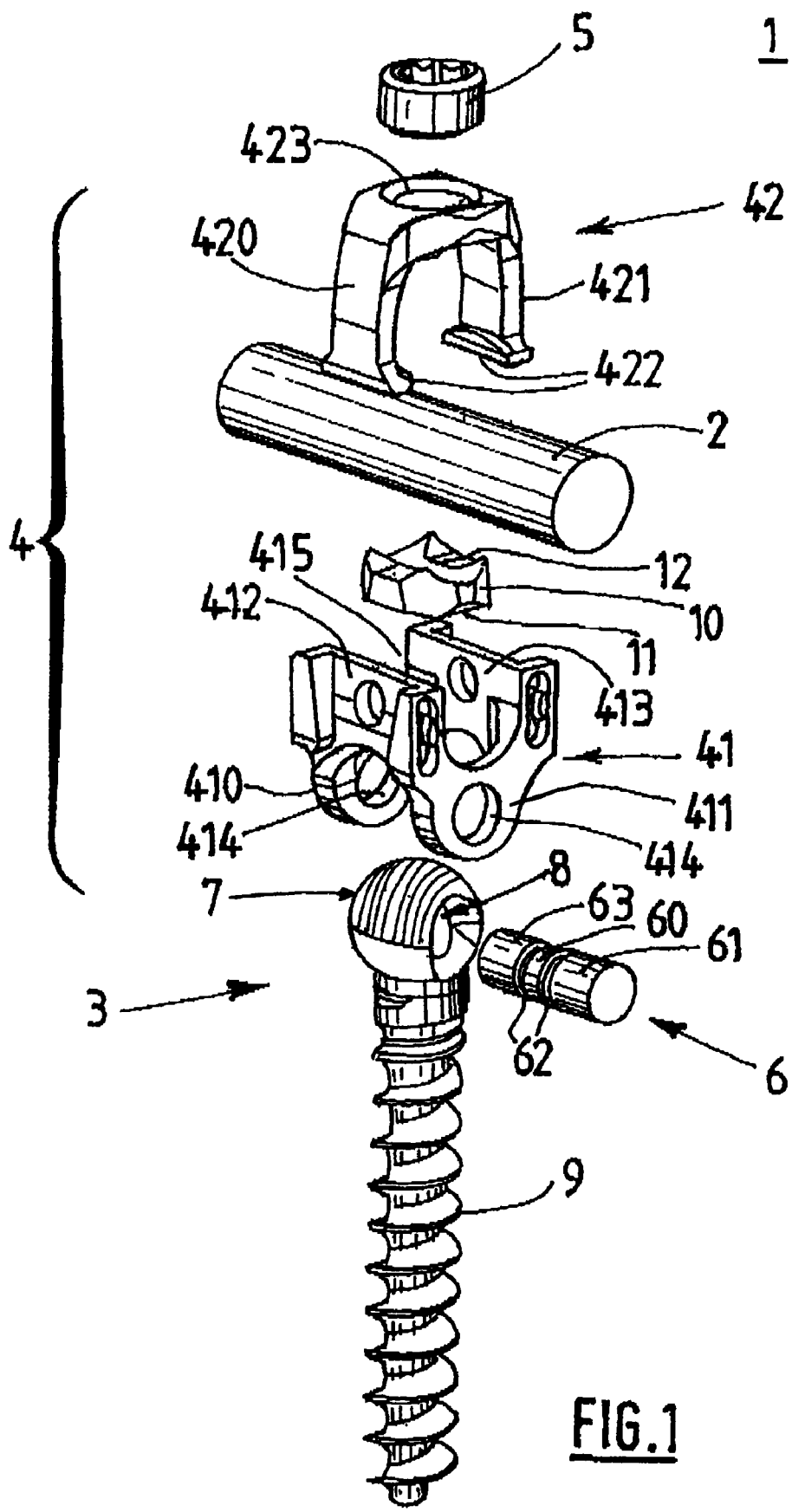
FIG. 1 is an exploded perspective view of a connector device and of a coupling rod in a first embodiment of the invention.

FIG. 1 is an exploded view of a connector device (1) of the invention for spinal osteosynthesis. Said connector device (1) is shown with a vertebrae coupling rod (2).

Said connector device (1) comprises bone anchor means (3) and a connector (4) for connection to a coupling rod (2). Said device (1) further comprises tightening means (5) for immobilizing the anchor means (3) and the connector (4) holding the coupling rod (2).

Advantageously, said bone anchor means (3) consists of a bone screw (3) made up of a threaded portion (9) and, at one of its ends, of a spherical head (7). The head (7) of said screw (3) is provided with a cavity (8) designed to be passed through a cylindrical pin (6). The coupling between the cavity (8) and the pin (6) is achieved in a manner such as to allow said pin (6) to turn in said cavity (8). For this purpose, the person skilled in the art can, in particular, act on the dimensions of the cavity (8) formed in the head (7) of the screw (3) and/or on the dimensions of said pin (6). For example, inlet bevels can be formed in the cavity (8) of the head (7) of the screw (3) in order to allow said pin (6) to be displaced angularly to a greater extent.

In addition, it is also possible to use a pin (6) presenting a non-plane surface, as explained in the description below in order to control the movement between said pin (6) and said cavity (8).

Over its circumference, said pin (6) advantageously has a convex central portion (60). Said central portion (60) is separated on either side from the end portions (61, 63) by respective grooves (62). Thus, when the pin (6) is positioned through the cavity (8) formed in the head (7) of the screw (3), the central portion (60) is disposed in said cavity (8).

The connector (4), which is designed to connect the coupling rod (2) to said screw (3), is made up of two pieces, namely a rod-receiving piece (41) and a closure piece (42).

The rod-receiving piece (41) is substantially U-shaped and it is constituted, in particular, by two branches (410, 411) substantially forming a clevis. Said branches (410, 411), disposed symmetrically relative to each other, are interconnected by interconnection side walls (412, 413).

The bottom end of each of said branches (410, 411) is provided with a respective hole (414), said holes (414) having cross-sections complementary to the cross-section of the pin (6), advantageously so that the pin is mounted in tight-fitting manner on the connector (4).

The gap between the ends of said branches (410, 411) that are provided with said holes (414) defines spacing sufficient to receive the head (7) of said screw (3) when the coupling rod (2) is assembled to the screw (3) via said connector (4), regardless of the angular position of said screw (3).

The top spacing defined by the U-shaped branches (410, 411) and the interconnection walls (412, 413) defines a recess (415) for receiving the coupling rod (2).

The closure piece (42) of said connector (4) is substantially U-shaped, and the ends of the branches (420, 421) of the U-shaped closure piece are provided with respective shoulders (422) that curve arcuately towards the inside of said branches (420, 421) of the U-shape. The dimensions and the shapes of the branches (420, 421) and of the shoulders (422) are determined so as to enable the closure piece (42) to be put in place and fitted over the rod-receiving piece (41).

In the seat formed between the branches (420, 421), the closure piece (42) is provided with a recess (423). Advantageously, said recess (423) is provided with tapping (not shown) for receiving said tightening means (5), which make it possible to lock said closure piece (42) permanently by tightening said tightening means (5).

A cradle-forming through intermediate element (10) is disposed between the rod-receiving piece (41) and the coupling rod (2). In its bottom face, said cradle element (10) has a concave zone forming a recess (11), said recess (11) being dimensioned to co-operate with the head of the screw (3). In the same way, in its top face, which is designed to receive said coupling rod (2), said through intermediate element (10) has a concave zone forming a second recess (12), said recess (12) being dimensioned to co-operate with said coupling rod (2).

So the resulting connector device is locked by means of the forces exerted between each of the elements. Thus, the tightening means (5) exert pressure on the coupling rod (2) which itself exerts pressure on the through intermediate element (10), which itself exerts pressure on the bone anchor means (3). The pin (6) passing through the head (7) of said screw (3) then exerts traction on rod-receiving piece (41) which itself exerts pressure on the closure piece (42) by means of the shoulders (422) of the closure piece (42) fastening into arches formed in the rod-receiving piece (41), the closure piece itself exerting traction on the tightening means (5) via the tapped recess (423).

Figure 2:
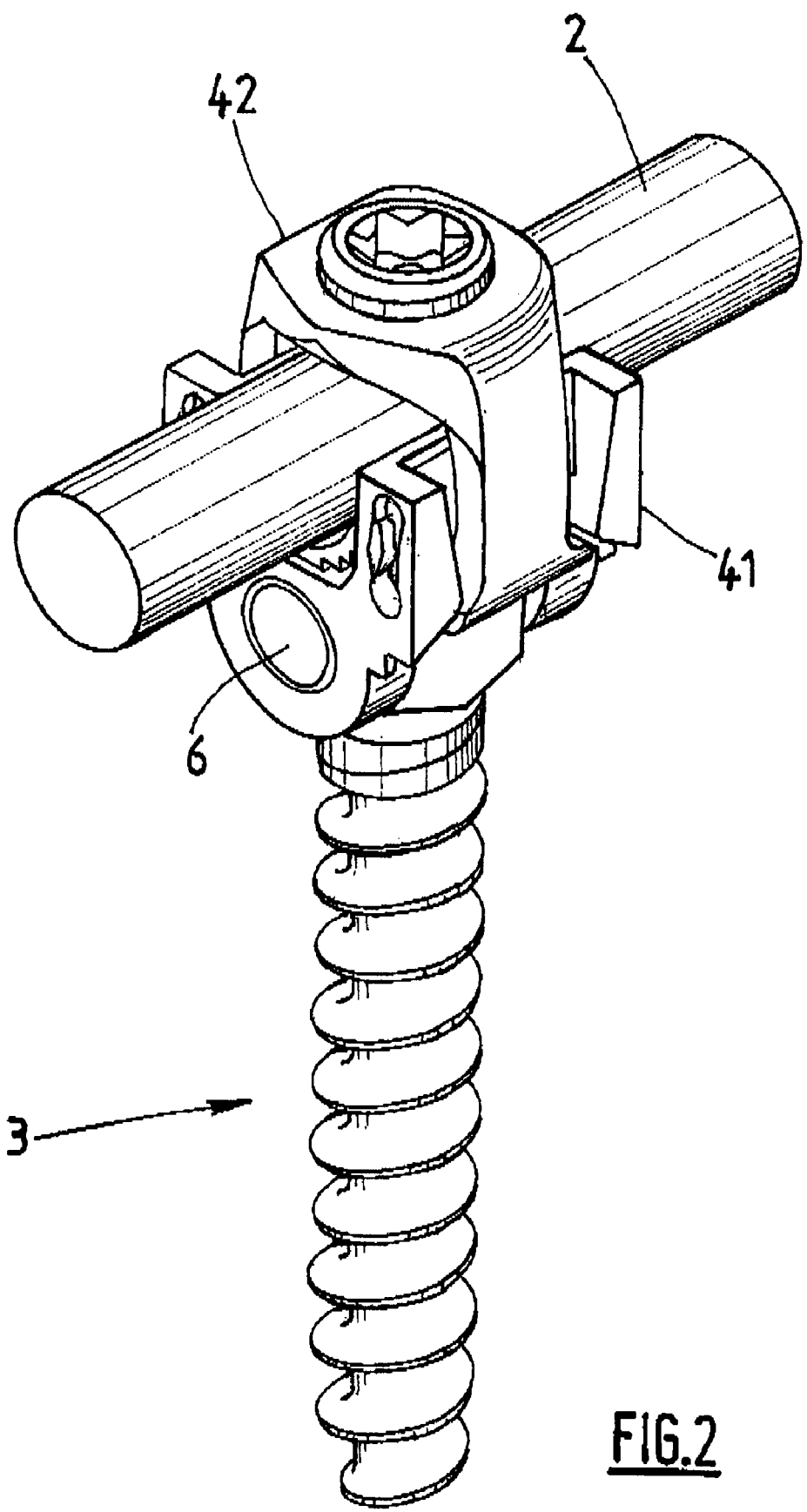
FIG. 2 is a perspective view of the connector device and of the coupling rod of FIG. 1 as assembled together.

FIG. 2 is a perspective view of the connector device (1) and of the coupling rod (2) of FIG. 1, as assembled together.

The connector (4) is assembled to the head (7) of the screw (3) by means of the pin (6) which passes through the head (7) of said screw (3) and co-operates with the two holes (414) provided in the branches (410, 411) of the connector (4), said branches (410, 411) being disposed on either side of said pin (6).

The closure piece (42) of said connector (4) is positioned over the complementary rod-receiving piece (41) so that the inside faces of the branches (420, 421) of said closure piece (42) are in contact with the interconnection walls (412, 413) of said rod-receiving portion (41). With the closure piece (42) closed over the rod-receiving piece (41) supporting the coupling rod (2), said coupling rod (2) is then held onto and associated with the screw (3).

Figure 3:
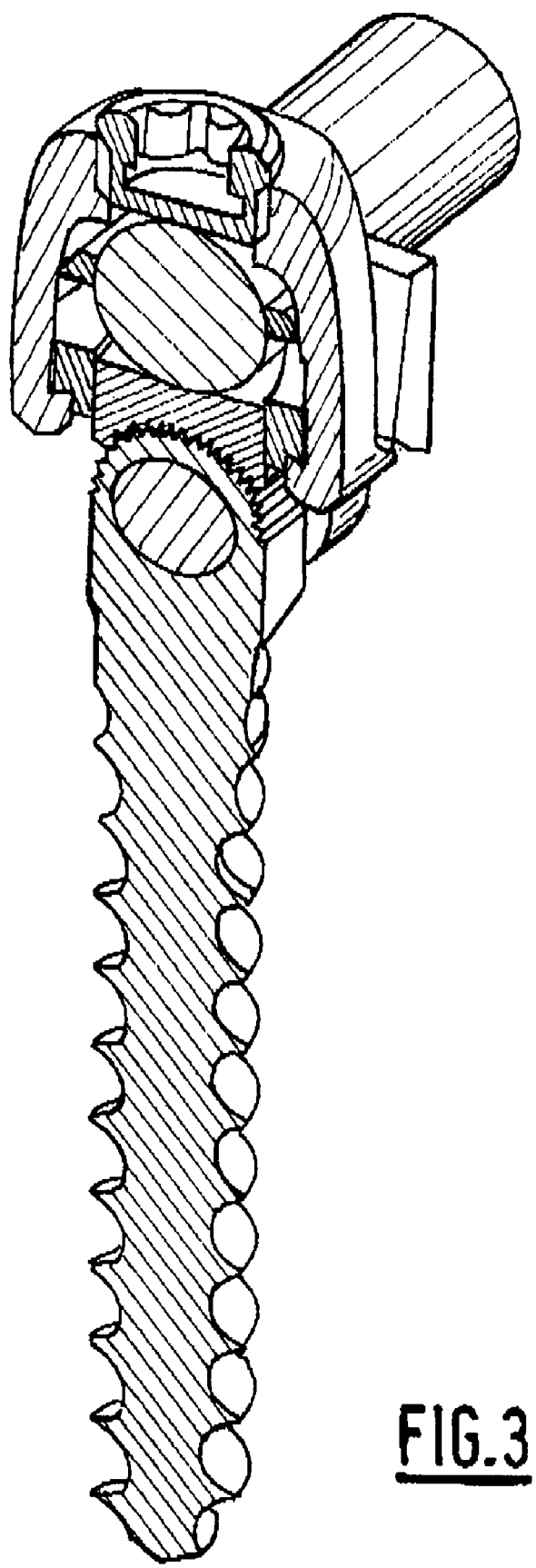
FIG. 3 is a perspective section view of the connector device of FIG. 2, with the coupling rod.

The interaction between the various elements forming the connector device (1) of the invention is shown in FIG. 3 which is a section view of said connector device (1) as assembled to the coupling rod (2).

In particular, FIG. 3 shows how the closure piece (42) is locked onto the rod-receiving piece (41) of said connector (4). The locking is achieved by means of the shoulders (422) of the closure piece (42), which shoulders are inserted into arches formed in the interconnection walls (412, 413) of said rod-receiving piece (41).

The resulting assembled connector device (1) makes it possible to enable the connector (4), while holding the coupling rod (2) securely, to be pivoted relative to said screw (3) in two directions, namely pivoting in a first direction parallel to the axial direction of the coupling rod (2) (frontal displacement of said connector (4) on said screw (3)), and pivoting on an axis perpendicular to the axial direction of said coupling rod (2) (sagittal displacement of said connector (4) on said screw (3)), it being possible for the sagittal pivoting to be increased by additional side pivoting. These various pivoting movements are shown in FIGS. 4 to 7.

Figure 4:
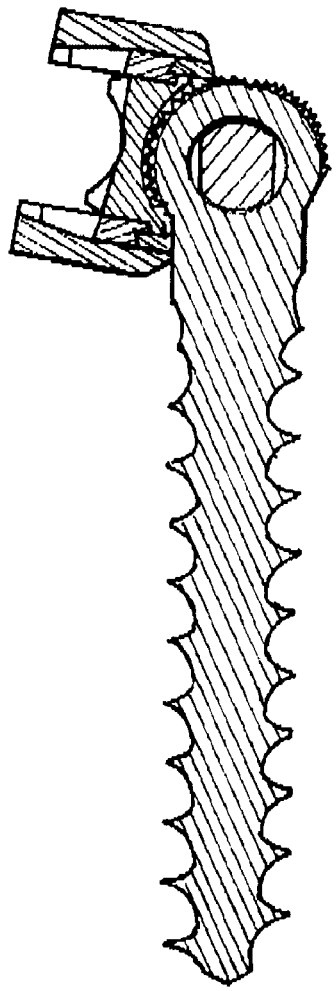
FIG. 4 is a side view of the connector device without the coupling rod, said connector device having been angularly displaced frontally.

In particular, the frontal displacement of said connector (4) on said screw (3) is shown in FIG. 4 which is a side section view of said connector device (1). In FIG. 4, in order to make it easier to understand operation, only the rod-receiving piece (41) of said connector (4), the through intermediate element (10) and said screw (3) are shown.

As explained above, by means of the respective dimensions and shapes of said pin (6) and of the cavity (8) formed at the head (7) of said screw (3), it is possible to generate at said pin (6) a movement in rotation perpendicular to the axis of the coupling rod (2) (sagittal displacement). And the rod-receiving portion (41) of said connector (4), which portion is fastened to said pin (6), pivots on the head (7) of the screw (3). By means of its configuration, the through intermediate element (10) follows the pivoting of the rod-receiving portion (41) relative to said screw (3) by sliding on the head (7) of said screw (3) on which said through intermediate element (10) rests.

Advantageously, the fontal displacement can be up to 180 degrees.

Figure 6:
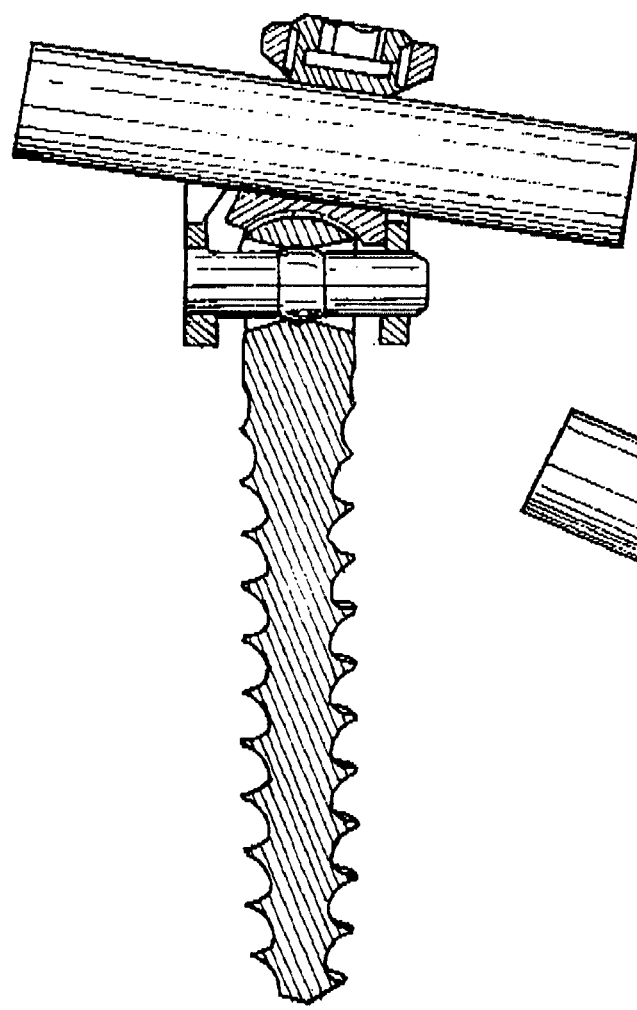
FIG. 6 is a face-on axial section view of the connector device of FIG. 5, as provided with the coupling rod, the connector device having been angularly displaced sagittally.
Figure 7:
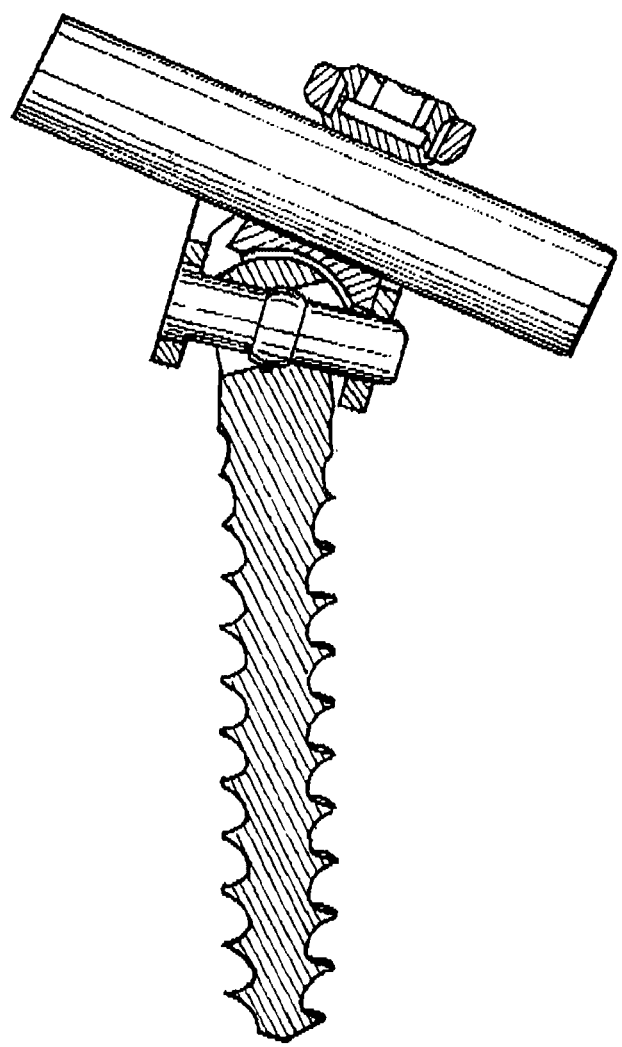
FIG. 7 is a face-on axial section view of the connector device of FIG. 5 provided with the coupling rod, said connector device having been angularly displaced sagittally to its maximum extent.

The sagittal pivoting is shown in FIGS. 6 and 7, which are face-on section views of the connector device (1) of the invention with a coupling rod (2). The sagittal pivoting can, as specified above, take place in two independent or combined movements.

Figure 5:
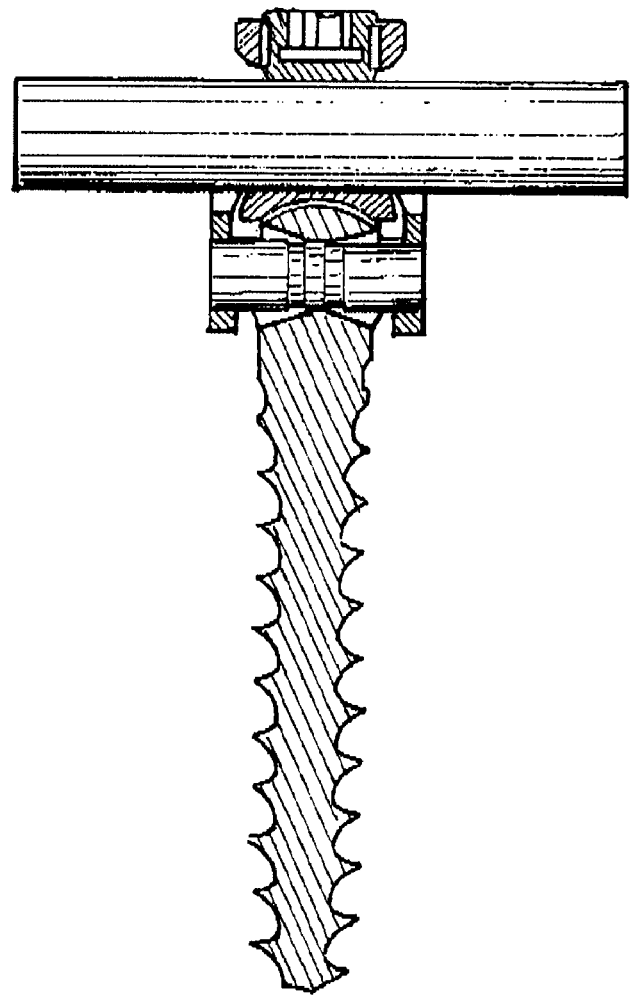
FIG. 5 shows a face-on axial section view of the connector device and of the coupling rod of FIG. 2.

In order to understand properly the two sagittal movements that can take place, FIG. 5 shows a face-on section view of said connector device (1) in the plane position. In this position, it appears that the pin (6) passing through the head (7) of the screw (3) has an axial direction parallel to the axial direction of the coupling rod (2).

From this rest position, a first pivot movement of said coupling rod (2) can be obtained by sliding the through intermediate element (10) on the head (7) of said screw (3) on which said through intermediate element (10) stands (FIG. 6). The first movement can be supplemented, as shown in FIG. 7, by a second pivot movement associated with pivoting of the convex portion (60) of the pin (6) in the cavity (8) of the head (7) of the screw (3). In the same way as the axial direction of the coupling rod (2) is modified during the first pivot movement, a change in the axial direction of said pin (6) also ensues.

Naturally, although not shown, the pivot movement of the pin (6) can be achieved independently from a pivot movement of said through intermediary element (10) and can be added to said movement preferably to reach an angular displacement of 60 degrees.

In order to control the pivot movements, be they frontal pivot movements or sagittal pivot movements, it is advantageous to propose coupling surfaces that are not necessarily smooth, but rather that advantageously present pieces in relief.

Figure 10:
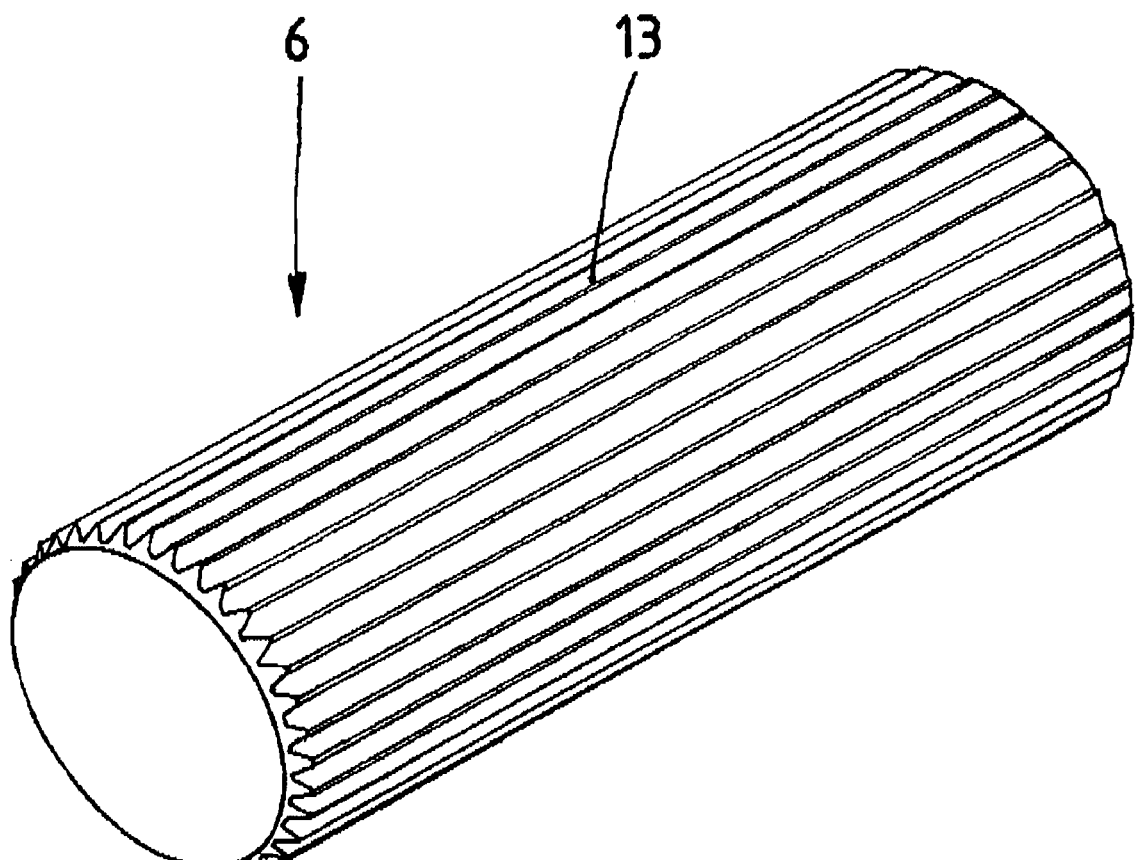
FIG. 10 is a perspective view of a pin passing through the connector device in a variant of the invention.

In particular, it is advantageous, as regards the frontal pivot movement, to use a pin (6) provided with longitudinal fluting (13). The fluting is distributed over its entire surface or over at least a portion of its surface that is to be disposed in the cavity (7) of said screw (FIG. 10).

Figure 11:
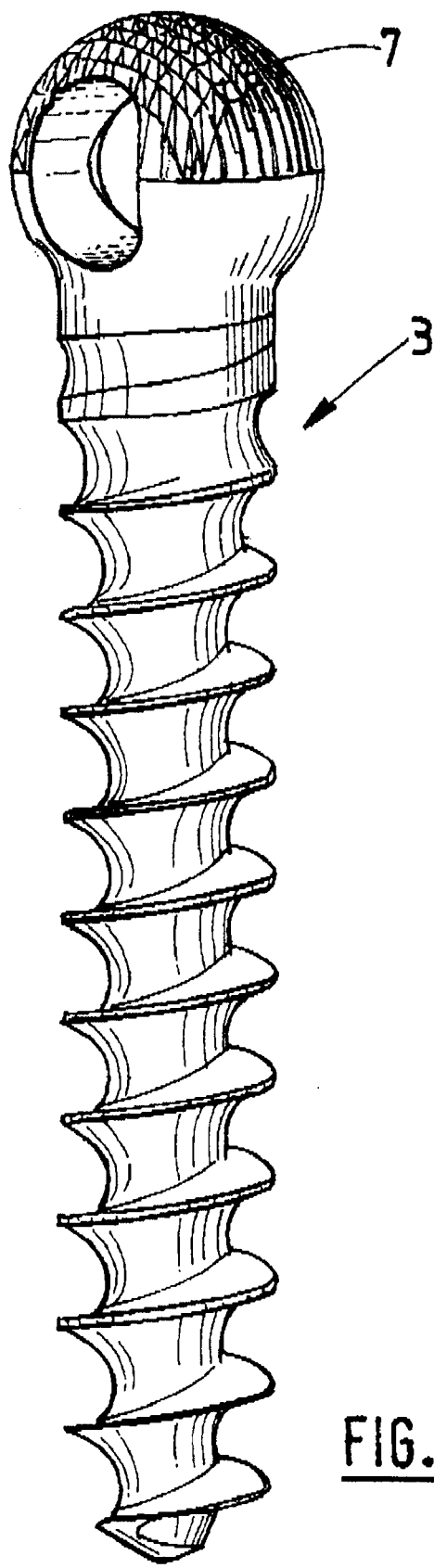
FIGS. 11 and 12 are perspective views of anchor means of the connector device in respective variant embodiments of the invention.
Figure 12:
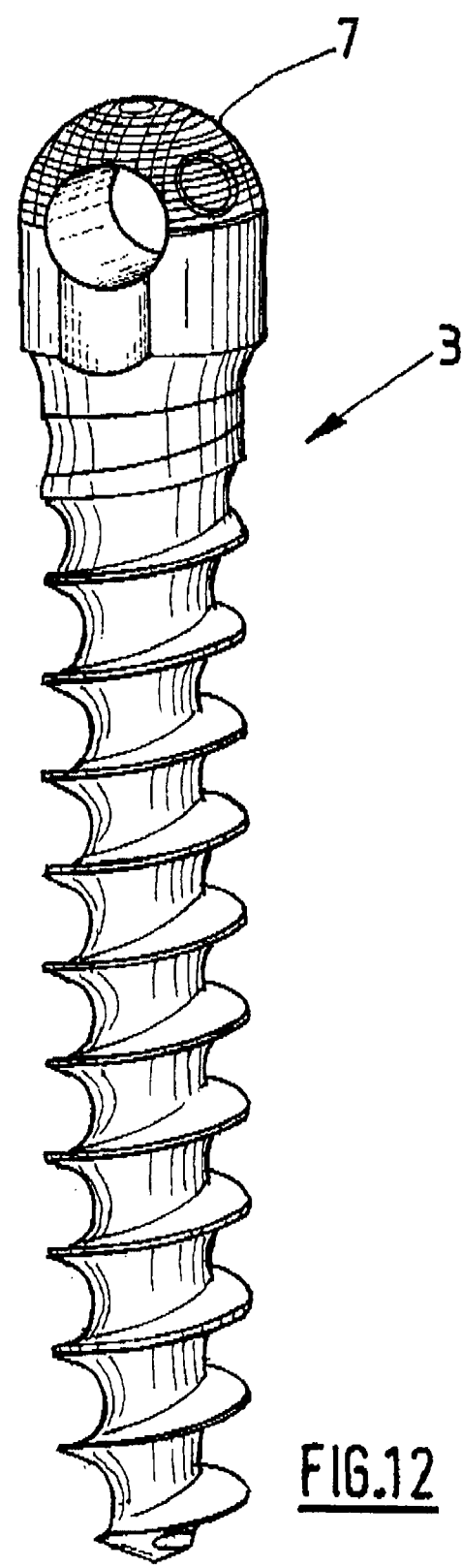

It is also advantageous for said screw (3) to be fluted or serrated as shown in FIGS. 11 and 12.

Figure 8:
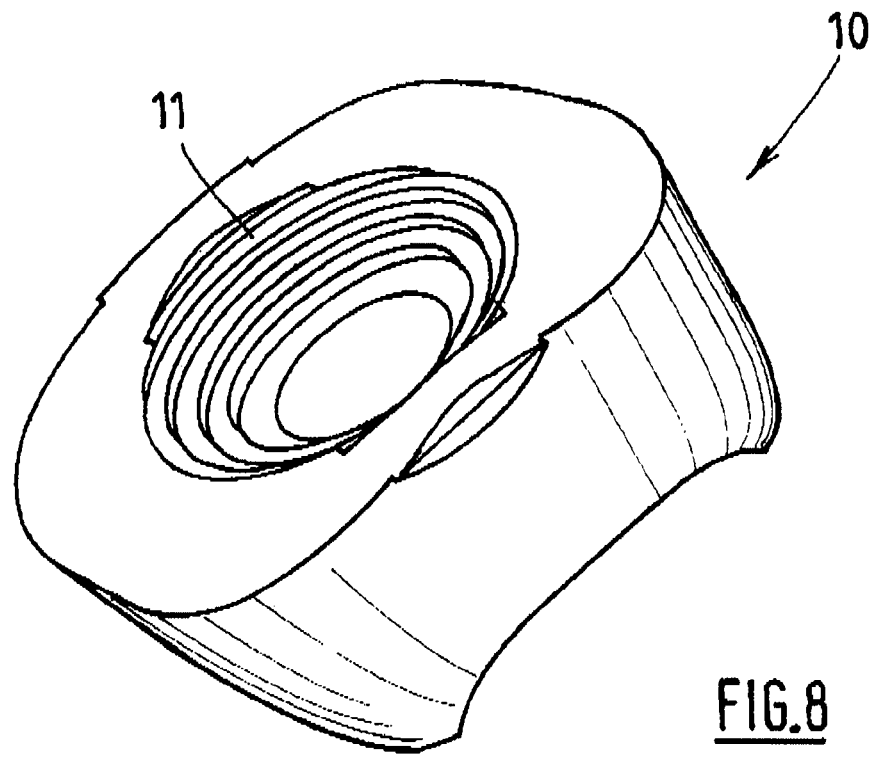
FIGS. 8 and 9 are perspective views showing a cradle-forming element of the connector device in respective variant embodiments of the invention.
Figure 9:
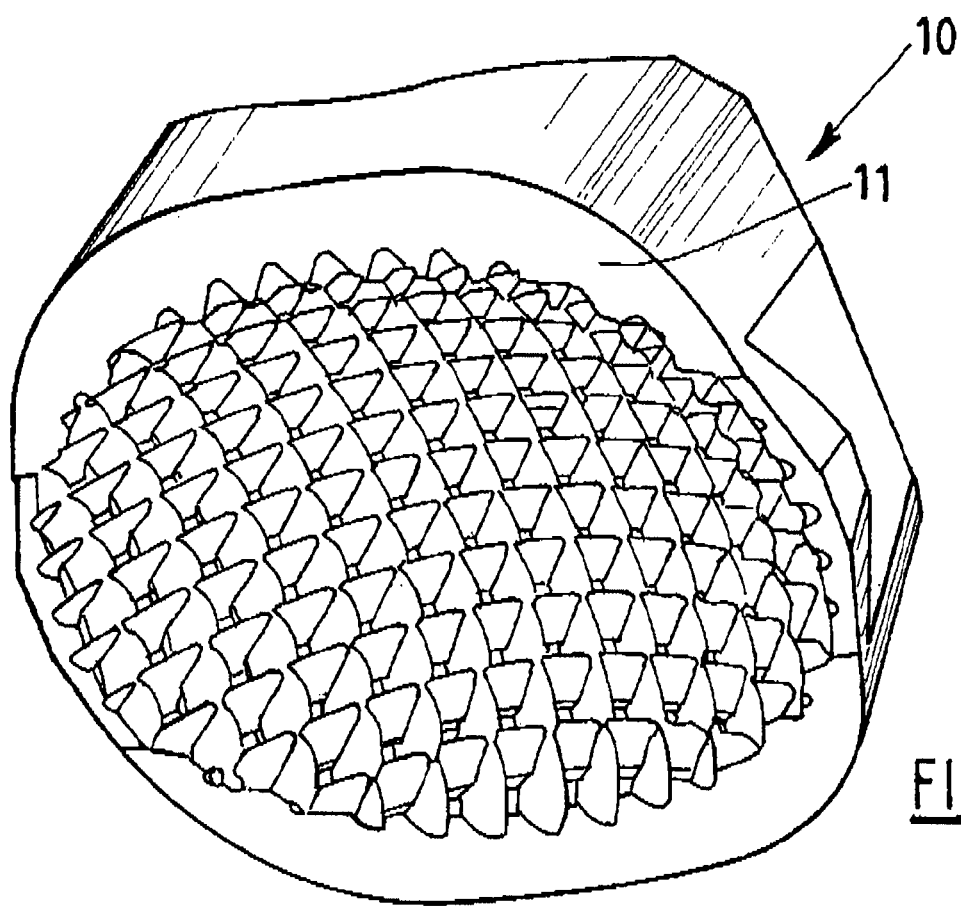

Similarly, the through intermediate element (10) can have a serrated or fluted zone over the surface in contact with the head (7) of said screw (3) (FIGS. 8 and 9).

Figure 13:
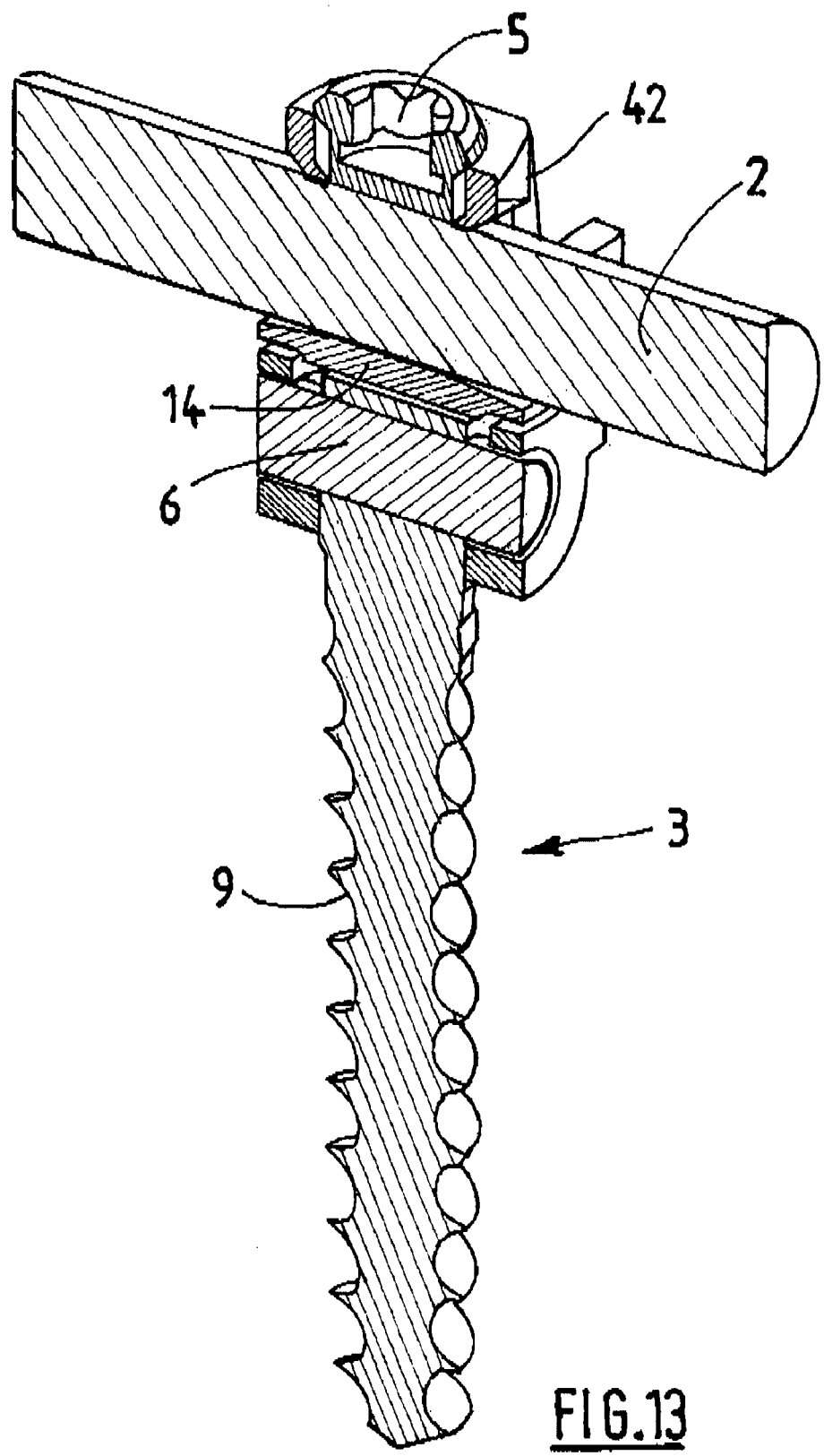
FIG. 13 is a perspective section view of the connector device as provided with a coupling rod in another embodiment of the invention.

FIG. 13 is a perspective section view of the connector device (1) as provided with a coupling rod (2) in another embodiment of the invention.

In this embodiment, said connector device (1) comprises anchor means which is a screw (3), a connector (4), and tightening means (5).

Advantageously, said rod-receiving piece (41) has a convex bearing surface (14) on which the coupling rod (2) is disposed. The pivot movement obtained by means of the through intermediate element (10) in the preceding embodiment is then obtained by the coupling rod (2) tilting on said bearing surface (14). In this embodiment, the screw (3) thus remains free to turn frontally after tightening, and the forces act as follows between the component elements of the connector device (1): the tightening means (5) exert pressure on the coupling rod (2), which itself exerts pressure on the bearing surface (14) of the rod-receiving piece (41), which exerts traction on the closure piece (42), which itself exerts traction on the tightening cap (5).

The invention is described by way of example above. Naturally, the person skilled in the art can implement various variants of the invention without going beyond the ambit of the patent.

The invention claimed is:

1. A connector device for spinal osteosynthesis, said connector device comprising bone anchor means, a connector designed to receive a coupling rod and assembled to one end of the anchor means, said connector being pivotable relative to said bone anchor means in a first direction parallel to an axial direction of said coupling rod and in a second direction on an axis perpendicular to the axial direction of said coupling rod, and tightening means for immobilizing the coupling rod, the connector and the anchor means being assembled together by a pin passing through the anchor means, said pin constituting a pivot coupling, and stabilization means for stabilizing the connector relative to the anchor means in a plane containing the rod and the anchor means when implanted in the patient, and wherein said pin has a fixed integral peripheral convex portion forming a portion of an exterior surface of said pin and which convex portion of the pin is disposed inside said anchor means so as to enable said anchor means to move over an angular displacement on said pin, wherein said stabilization means are constituted by said pin having an axial direction parallel to an axial direction of said coupling rod, allowing a degree of axial rotation only, to the exclusion of tilting in a plane perpendicular to the rod.

2. A connector device according to claim 1, wherein the connector co-operates with said pin with a degree of rotation relative to an axial direction, and a degree of angular displacement relative to at least one perpendicular direction.

3. A connection device for spinal osteosynthesis according to claim 2, wherein the connector co-operates with said pin with an amplitude of rotation relative to the axial direction lying in the range 90° to 180°.

4. A connector device for spinal osteosynthesis according to claim 2, wherein an amplitude of the angular displacement relative to the at least one perpendicular direction lies in the range 20° to 60°.

5. A connector device according to claim 1, wherein the convex portion of the pin is such that it enables a mutual angular displacement of said pin and said anchor means relative to a direction perpendicular to said pin.

6. A connector device according to claim 5, wherein the convex portion of the pin presents convexity distributed uniformly over the circumference of said pin in order to enable said pin to move over a sagittal angular displacement on said anchor means.

7. A connector device according to claim 1, wherein the convex portion of the pin presents convexity distributed uniformly over the circumference of said pin in order to enable said pin to move over a frontal angular displacement on said anchor means.

8. A connector device according to claim 1, wherein said connector has a bearing surface on which the coupling rod bears, said bearing surface being configured in a manner such as to enable said coupling rod to move over an additional sagittal angular displacement relative to said anchor means.

9. A connector device according to claim 8, wherein said bearing surface is concave in shape.

10. A connector device according to claim 9, wherein a through element consists of a cradle-forming through element enabling said coupling rod to move over the sagittal angular displacement relative to said connector.

11. A connector device according to claim 8, wherein said bearing surface consists of a cradle-forming element disposed in the connector, said cradle-forming element having a bottom recess co-operating with the connector in a manner such as to enable the additional sagittal angular displacement to take place, and a top recess designed to receive the coupling rod.

12. A connector device according to claim 1, wherein an intermediate element receiving said coupling rod passes through the connector, said through intermediate element having a bottom recess co-operating with the end of said anchor means in a manner such as to enable all of the degrees of freedom of rotation of said device to be locked.

13. A connector device according to claim 12, wherein said through intermediate element has a top face of concave shape enabling said coupling rod to move over the sagittal angular displacement relative to said connector.

14. A connector device according to claim 12, wherein the bottom recess of said through intermediate element presents at least one serrated or fluted zone.

15. A connector device according to claim 12, wherein the end of the anchor means is serrated or fluted over its entire surface or over a portion thereof.

16. A connector device according to claim 1, wherein said pin has longitudinal fluting over all or some of its surface.

17. A connector device according to claim 1, wherein said pin passes through the end of the anchor means and co-operates with two holes provided in branches of the connector, said holes presenting cross-sections complementary to a cross-section of the pin, and said branches being disposed on either side of said pin.

18. A connector device according to claim 1, wherein the anchor means are constituted by a screw which has a threaded portion, and a spherical head provided with a cavity for receiving said pin in part.

19. A connector device according to claim 1, wherein the connector is constituted by a substantially U-shaped rod-receiving piece designed to receive one end of said anchor means as provided with the pin and with the coupling rod, and of a closure piece that comes to engage over the rod-receiving piece in order to hold the coupling rod onto the rod-receiving portion of said connector by using said tightening means.

20. A connector device for spinal osteosynthesis, said connector device comprising bone anchor means, a connector designed to receive a coupling rod and assembled to one end of the anchor means, said connector being pivotable relative to said bone anchor means in a first direction parallel to an axial direction of said coupling rod and in a second direction on an axis perpendicular to the axial direction of said coupling rod, and tightening means for immobilizing the coupling rod, the connector and the anchor means being assembled together by a pin passing through the anchor means, said pin constituting a pivot coupling, and stabilization means for stabilizing the connector relative to the anchor means in a plane containing the rod and the anchor means when implanted in the patient, and wherein said pin has a fixed integral peripheral convex portion forming a portion of an exterior surface of said pin and which convex portion of the pin is disposed inside said anchor means so as to enable said anchor means to move over an angular displacement on said pin, wherein said stabilization means are constituted by said pin having an axial direction perpendicular to an axial direction of said coupling rod, and the device further comprising locking means for preventing the connector from moving pivotally on said anchor means.

21. A connector device according to claim 20, wherein the locking means consists of a piece passing through the connector, said through piece presenting a bottom face constituted by a recess co-operating with the end of said anchor means and a top face receiving said coupling rod, so as to enable all of the degrees of freedom of rotation of said device to be locked.

22. A connector device according to claim 21, wherein the top face is concave in shape.

23. A connector device according to claim 21, wherein the through piece consists of a cradle-forming element which, in its top face, has a recess for receiving said coupling rod.

24. A connector device according to claim 21, wherein the recess in the bottom face of said through piece is serrated or fluted at least in part.

25. A connector device according to claim 21, wherein the end of said anchor means that is in contact with the through piece is serrated or fluted at least in part.

26. A system for osteosynthesis on the spinal column, said system comprising at least one coupling rod and at least two connector devices according to claim 1, each of said connector devices being suitable for being anchored in a respective vertebra.

* * * * *